United States Patent [19]

Shaw, Jr.

[11] 4,381,001

[45] Apr. 26, 1983

[54] IUD ARRANGEMENT

[76] Inventor: Seth T. Shaw, Jr., 30036 Via Borica, Rancho Palos Verdes, Calif. 90274

[21] Appl. No.: 165,187

[22] Filed: Jul. 1, 1980

Related U.S. Application Data

[60] Division of Ser. No. 55,900, Jul. 9, 1979, which is a continuation-in-part of Ser. No. 928,093, Jul. 26, 1978, Pat. No. 4,233,968, Ser. No. 927,765, Jul. 25, 1978, and Ser. No. 928,106, Jul. 26, 1978, abandoned.

[51] Int. Cl.³ .............................................. A61F 5/46
[52] U.S. Cl. ................................... 128/130; 128/260; 128/270
[58] Field of Search ............................... 128/130–133, 128/260–270; 424/22, 17

[56] References Cited

U.S. PATENT DOCUMENTS

| | | | |
|---|---|---|---|
| 3,817,248 | 6/1974 | Buckles et al. | 128/260 |
| 4,144,317 | 3/1979 | Higuchi et al. | 424/21 |
| 4,215,200 | 7/1980 | Miyata et al. | 435/273 |

FOREIGN PATENT DOCUMENTS

| | | |
|---|---|---|
| 2247949 | 8/1972 | Fed. Rep. of Germany . |
| 2250520 | 6/1975 | France . |
| 2282262 | 3/1976 | France . |
| 47-11741 | 4/1972 | Japan . |
| 376806 | 7/1932 | United Kingdom . |
| 516289 | 12/1939 | United Kingdom . |
| 938042 | 9/1963 | United Kingdom . |

OTHER PUBLICATIONS

"Synthetic Enzyme Inhibitors as Antifertility Agents", Zanefeld, Fed. Eur. Biochem. Soc., 1970, 11(5), 345–347.
"Hemmung der Thrombin-, Plasmin-und Trypsinwirkungdurch Alkyl–und Alkoxybenzamidine", Markwardt et al., Berlin DD, pp. 551–554.
"Unlisted Drugs", vol. 24, #4, Catham, N.J., U.S., 1972, p. 57, Abstracts.
Merck Index, 9th Ed., #2060, p. 265.
"Synthese Antiproteolytisch Wirksamer Ester von Guanidinobenzoesäuren und Guanidinomethylbenzosäuren", Wagner et al., Bereich Pharm. Chem., 1973.
"Unlisted Drugs", Apr. 1972, vol. 24, No. 4, Catham, N.J., U.S., Abs.
"Intrauterine Medication with Epsilon Aminocaproic Acid", Contraception, 11:395, Shaw et al., 1975.
"Comparitive Studies of the Inhibition of Trypsin, Plasmin, and Thrombin", European J. Biochem., 6(1968), Markwardt et al., pp. 502–506.
"Inhibition of the Amidase and Kininogenase Activites by Aromatic Diamidines", Arch. Int. Pharmacodyn, 194, Geratz et al., 1971.
"Inhibitory Effect of Aromatic Diamides on Trypsin and Enterkinase", Experientia, 25/12, Geratz, 1969.
"Fibrin Proteolysis in the Monkey Uterine Cavity", Nature, 228:1097, Shaw et al., 1970.
"Effect of Tranexamie Acid in Menorrhagia with IUD's", J. Reprod. Med., 5:154, Westrom et al., 1970.
"Aminocaproic Acid and Menstrual Loss in Women Using IUD's", Brit. Med. J., 4:17–19, Kasonde et al., 1975.
"Studies of Menstrual Physiology", Medical Primatology, Shaw et al., Lyon, 1972, pp. 317–324.
"Uterine Bleeding in the Rhesus Monkey in Response to Various Designs of IUD's", Fert. Steril., 25(4):358, Shaw et al., 1974.
"Studies on Menstrual Blood Loss in Intact and Experimental Rhesus Monkeys", J. Med. Prim., 2:153, Poon et al., 1973.
"Inhibition of Thrombin, Plasmin, Plasiminogen Activation by Amidino Compounds", Throm. Diath. Haemorrh., 23(3): 486–499, Geratz, 1970.
"Inhibition of Coagulation and Fibrinolysis by Aromatic Amidino Compounds", Theomb. Diath. Haemorrh., 25:391, Geratz, 1971.
"Effect of Ethamsylate and Aminocaproic Acid on Menstrual Blood Loss in Women Using IUD's", Brit. Med. J., Kasonde et al., Oct. 1975.
"Synthetische Hemmstoffe des Plasmins", Fibrinolyse, Landmann, Budapest, 1969.
"Comparitive Inhibition of Thrombin, Plasmin, Trypsin", J. Med. Chem., vol. 16, Coats, 1973.
"Structure–Activity Relationships for the Inhibition of Plasmin and Plasminogen Activation", Thrombos. Diathes. Haemorrh., (Stuttg), Geratz, 1973.

Primary Examiner—Richard J. Apley
Assistant Examiner—T. J. Wallen
Attorney, Agent, or Firm—Don B. Finkelstein

[57] ABSTRACT

A medicated intrauterine device insertable in and retained in the uterus for a predetermined time period and having a drug with a controlled release rate and said drug comprising a guanidine such as an aromatic monoguanidine, an aromatic diguanidine, a non-aromatic monoguanidine or a non-aromatic diguanidine to provide anti-fibrinolytic, anti-proteolytic and/or anti-conceptive action. The drug is one or a mixture of more than one of such guanidines, or a mixture of one or more of such guanidines with one or more amidines.

17 Claims, 5 Drawing Figures

IUD ARRANGEMENT

REFERENCE TO RELATED APPLICATIONS

This application is a division of co-pending United States patent application Ser. No. 055,900, filed July 9, 1979, which is a continuation-in-part of application Ser. No. 928,093, filed July 26, 1978, now U.S. Pat. No. 4,233,968, issued Nov. 18, 1980, United States patent application Ser. No. 927,765, filed July 25, 1978, and United States patent application Ser. No. 928,106, filed July 26, 1978, now abandoned, and is related to U.S. Pat. No. 4,284,074, issued Aug. 18, 1981, and United States patent application Ser. No. 055,903, filed July 9, 1979, and to United States patent application Ser. No. 165,376, filed June 23, 1980, which is a division of United States patent application Ser. No. 055,900, filed July 9, 1979. The teaching and technology of each of the above identified patents and patent applications is incorporated herein by reference.

BACKGROUND OF THE INVENTION

1. Field of the Invention

This invention relates to the medicated intrauterine device art, and more particularly to an improved intrauterine device providing a contraceptive, anti-fibrinolytic, and anti-proteolytic action when inserted in the uterus.

2. Description of the Prior Art

Many forms and configurations of intrauterine devices designed to prevent conception in the female have heretofore been utilized. Such devices have been provided in a variety of shapes, such as the "T" device shown in U.S. Pat. No. 3,533,406, the Loop, such as shown in U.S. Pat. No. 3,200,815, a "Y" configuration, generally termed a "Ypsilon" configuration, a ring or modified ring such as the OTa ring, and many modifications thereto, including flat, leaf-like members between various segments of the intrauterine device. Such intrauterine devices which were not provided with any medications associated therewith depended upon their presence in the uterus to prevent conception.

Further, other intrauterine devices (IUDs) have incorporated a controlled release rate medication or drug therein to further aid the anticonceptive action thereof. Such medicated IUDs have generally employed copper or progesterone as the contraceptive or antifertility agent. However, it has been found that copper-releasing intrauterine devices, as well as non-medicated intrauterine devices still resulted in pain and cramping to the wearer, as well as metrorrhagia and menorrhagia. Consequently, the excessive uterine hemorrhage, with or without pain, continues to be a leading cause for this type of intrauterine device removal. The progesterone-releasing intrauterine devices are associated with significantly less bleeding than other devices but they appear to be associated with a serious complication apparently produced by the release of progesterone. This complication is ectopic pregnancy.

Nevertheless, the general convenience and safety of intrauterine devices continues to give hope that the IUD may one day provide an ideal method for worldwide population control, since it has been found, statistically, that intrauterine devices can provide effective contraception in a 98-99% range of effectivity, they do not require conscious effort, are less subject to human failings than any other type of contraceptive, their antifertility effect is completely reversible, they have minimal, if any systemic effect, and their effect is confined essentially to the uterus. However, it is believed that even greater antifertility effect can be achieved by utilizing other anticonception agents with an IUD, which agents do not have the serious detrimental side effects noted above.

Consequently, there has been a need for improved medicated intrauterine devices providing greater antifertility effect and in which the side effects of pain, metrorrhagia and/or menorrhagia are reduced or eliminated, and which are not associated with other serious side effects such as ectopic pregnancy.

While the inflammatory response of the endometrium to intrauterine devices has heretofore been known, I have discovered that the chronic response of the endometrium to longterm intrauterine device exposure is more a humoral type of reaction (accompanied by increased vascular permeability with edema and interstitial hemorrhage) than the immunologic or cellular type of response (accompanied by infiltration of immune complexes or of leukocytes, such as plasma cells or neutrophils). However, I have found that there are defects in small endometrial vessels which suggest damage caused by mechanical distortion of the uterine tissues. The defects generally lack hemostatic plugs of platelets and/or fibrin. Further, there is evidence that fibrinolysis is activated in the uterus in response to the presence of an intrauterine device. This activation could result in blockage of normal hemostatic reaction at several levels in the coagulation system. Further, it may initiate, aid, or aggravate humoral inflammation by any one or all of the following mechanisms:

1. Activation of the complement system and histamine release;
2. Activation of prekallikrein; and
3. Release of fibrin degradation fragments.

Histamine can cause vascular dilation and increase vascular permeability. Kallikrein (activated prekallikrein) releases bradykinin which can have an effect similar to histamine and may also cause cramping and pain. Fibrin degradation fragments may enhance the vascular effects of histamine and bradykinin. Combined with distortion of the endometrium caused by myometrial contractility around the relatively inelastic or unyielding IUD, which may also be associated with increased prostaglandin synthesis and release, it may be predicted that excessive bleeding from leaky or broken vessels will occur. For these reasons, incorporation into medicated IUD devices of potent inhibitors of plasminogen activation and plasmin activity (fibrinolytic activity) for the purposes of intrauterine release over an extended time period can provide an alleviation of the aforesaid undesired effects.

It has also heretofore been found that IUD associated uterine hemorrhage can be alleviated by the systemic (oral) intake of the fibrinolytic inhibitors epsilon aminocaproic acid (EACA) and tranexamic acid. I have also demonstrated that an EACA loaded IUD inserted into the uterus of rhesus monkeys provides an ameliorative effect on menstrual blood loss, and there was no apparent systemic effect by such medicated devices on fibrinolytic activity in these animals. However, neither EACA nor tranexamic acid would appear to be satisfactory agents for long-time intrauterine medication. First, they are not highly potent anti-fibrinolytic agents and would have to be delivered at a rather high rate into the uterine cavity. Thus, a drug loaded IUD would become exhausted of its medication in a short period of time, or would require an unacceptably large size of device. In addition, EACA and tranexamic acid are small molecules which are highly diffusible and water soluble. Therefore, intrauterine release thereof from a medicated intrauterine device at a steady, constant rate is difficult to control and effective concentrations inside the uterus difficult to maintain. Consequently, inhibitor concentrations of either EACA and tranexamic acid of between $1 \times 10^{-3}$ and $1 \times 10^{-4}$ Mol/liter, which is the concentration of these drugs required to be effective, respectively, over a prolonged period of time is generally not achievable considering the amount of medication which is feasible to load into an IUD and considering the diffusion and solubility properties of these compounds and the rate of water turnover inside the uterus.

While there heretofore has been some indication that certain compounds used for treatment of protozoal, bacterial and fungal infections, may have antifibrinolytic properties, there has not heretofore been any indication of anti-fertility action of these compounds added to an intrauterine device. These compounds may be generally defined as the aromatic amidines, and in particular, the aromatic diamidines. However, heretofore, it has not been specifically recognized that their anti-fibrinolytic action inside the uterus can alleviate the metrorrhagia and menorrhagia. Further, even though such metrorrhagia and menorrhagia may be alleviated, the pain and cramps associated with intrauterine devices could still remain a major drawback to effective extensive use of medicated intrauterine devices as a population control technique.

Additionally, in many prior art IUDs, expulsion thereof is a somewhat frequent occurrence. Such undesired expulsion is another drawback of prior art IUDs.

Consequently there has long been a need for a medicated intrauterine device which not only enhances the anti-fertility action of the IUD but also provides reduction or elimination of metrorrhagia or menorrhagia for an extended period of time, as well as decreasing the pain and cramps associated with wearing an intrauterine device, as well as decreasing the tendency of expulsion thereof.

In my above mentioned co-pending patent application Ser. Nos. 927,765, 928,093, and 928,106 I have disclosed the structure associated with the use of the amidines such as the aromatic and non-aromatic monoamidines and diamidines for utilization in connection with an IUD to provide the above desiderata. However, I have also discovered that the guanidines, such as aromatic monoguanidine, aromatic diguanidines, non-aromatic monoguanidines and non-aromatic diguanidines also can provide the above desiderata.

SUMMARY OF THE INVENTION

Accordingly, it is an object of the present invention to provide an improved intrauterine device.

It is another object of the present invention to provide an improved medicated intrauterine device of the type enhancing the anti-fertility action of the intrauterine device.

It is yet another object of the present invention to provide an improved medicated intrauterine device which reduces metrorrhagia and menorrhagia.

It is yet another object of the present invention to provide an improved intrauterine device that reduces pain and cramps associated with the utilization of an intrauterine device as well as minimizing the expulsion thereof.

As set forth in my above mentioned co-pending patent applications Ser. Nos. 927,765, 928,093 and 928,106, the antiproteolytic action and, in particular, the anti-fibrinolytic action of the aromatic monoamidines, aromatic diamidines and non-aromatic diamidines can provide a reduction in metrorrhagia and menorrhagia because of the particular characteristics associated with the reaction of the endometrium and/or the fluid of the uterus to the presence of an intrauterine device. Further, it is believed that inhibition of other proteolytic systems in the endometrium and/or muscle wall of the uterus can reduce and/or eliminate the pain and cramps associated with wearing an intrauterine device, as well as minimizing the risk of expulsion thereof. The amidines and, in particular, the aromatic monoamidines, aromatic diamidines, and non-aromatic diamidines, have been found to possess the desired properties, due to the antifibrinolytic and other anti-proteolytic effect thereof, to reduce or eliminate metrorrhagia and/or menorrhagia.

There has not, heretofore, been any recognition that the guanidines have an anti-proteolytic action, and an anti-fibrinoly action in the uterus, or an anti-bleeding action, or an anti-fertility action. I have discovered, however, that the guanidines, in addition to the amidines, do have such properties and, it is believed, may have even more potent effects.

Thus, I have discovered that there is a surprising and unexpected result in utilization of guanidines with intrauterine devices in that they may decrease IUD induced uterine bleeding and enhance the anti-fertility effect of the IUD by providing an anti-proteolytic and, particularly, an anti-fibrinolytic action in the uterus. Each treated IUD, therefore, may additionally cause a greater contraceptive effect than has heretofore been obtainable with the above-mentioned prior art IUDs of either the plain or medicated type. This unexpected result, it is believed, is achieved by the mechanism of the guanidine acting upon the fertilized egg or the blastocyst (preimplantation embryo) to cause it to degenerate. The guanidine could, in addition act on the sperm to either kill or render them ineffective in fertilization.

Further, it is believed, that certain anti-proteolytic action of the guanidines could reduce or eliminate the pain and cramps often associated with wearing an IUD.

According to a preferred embodiment of the present invention, a uterus insertable body member is provided. The body member may be of any desired shape or configuration of an intrauterine device such as those heretofore utilized, or any other configuration. A drug which may be one or more drugs selected from the class consisting of aromatic monoguanidines, aromatic diguanidines, nonaromatic monoguanidines and non-aromatic diguanidines or a mixture of one or more guanidines with one or more amidines, is provided with the body member in such a fashion that its release rate over an extended period of time is controlled within predetermined limits. As utilized herein, the term "drug" refers to either a single one of the above mentioned guanidines or a mixture of more than one of the guanidines, or mixture of one or more of the amidines as set forth in my co-pending patent application Ser. Nos. 927,765, 928,093 and 928,106, with the guanidine of the present invention. The body member of the intrauterine device may be a polymer matrix fabricated in any of the above mentioned shapes or configurations from, for example, polyethylene, and the drug may, in this embodiment, be a simple mixture with the polymer matrix. The shape, charge, and other characteristics such as hydrophobicity of the molecule of the drug, as well as the characteristics of the polymer matrix of the body member can be adjusted to determine the rate of drug release from the device when placed within the uterus to achieve a desired rate of emission of the drug over a predetermined time period by known techniques.

In another embodiment of the present invention, the drug is provided as a biodegradable polymer or copolymer with, for example another amidine, guanidine and/or epsilon aminocaproic acid, and mixed with the supporting polymer matrix of the body member.

In yet another embodiment of the present invention, the drug may be provided in a biodegradable polymer or copolymer, and bonded covalently or non-covalently to the polymer matrix of the device either within or on the surface of the polymer matrix of the body member.

Additionally, in yet other embodiments of the present invention, the above mentioned embodiments may be combined with a surface coating on the body member wherein the surface coating comprises a biodegradable cross-linked polymer or copolymer of the drug bonded covalently to the surface. Such embodiments may provide a soft hydrogel coating which enhances the tolerance of the walls of the uterus to enhance the retention of the medicated intrauterine device in the uterus during the time period soon after insertion. It has been found that the undesired expulsion often occurs during this time period.

In yet another embodiment of the present invention, which may be combined with any of the above mentioned embodiments, a coating is provided on some or all of the surfaces of the body member. The coating may be covalently bonded to the surface of the body member and consists of a non-biodegradable monomer, dimer, oligomer, or cross-linked polymer of the drug. Such embodiment provides a prolonged surface effect for reducing deleterious effects on the uterine wall, as well as provides the desired prolonged release of the drug from the body member. The bleeding of the endometrium in contact with the intrauterine device is at the surface of the endometrium. The inhibition of plasminogen activator and plasmin by solid phase enzyme inhibition such as the surface linked drugs described in this paragraph constantly during the duration of wearing of the intrauterine device could lead to a lessening of the bleeding at the interface between the endometrium and the intrauterine device.

In another embodiment of the present invention, the surface of the body member of any one of the above-defined embodiments may be partially covered by metallic copper to provide additional anti-conceptive action for the device.

The drug may be utilized either in its base form, or as certain esters such as isethionate, or as certain salts, such as hydrochloride or phosphate, depending upon the degree of solubility desired in the uterine fluid for control of release rate and tissue uptake of the drug, as well as enhancing the effectiveness of the particular compound employed.

In those embodiments of the present invention wherein a drug is provided as a coating on the surface of the IUD, the body member of the IUD may also incorporate a drug according to the principles of the present invention mixed therewith or the drug may be provided only in the coating. In those embodiments wherein a drug is provided as a coating on the surface of the IUD and a drug is also incorporated in the body member, the drug of the coating may be the same as the drug in the body member or they may be different drugs.

BRIEF DESCRIPTION OF THE DRAWING

The above and other embodiments of the present invention may be more fully understood from the following detailed description taken together with the accompanying drawing wherein similar reference characters refer to similar elements throughout and in which.

DESCRIPTION OF THE PREFERRED EMBODIMENTS

Figure 1:
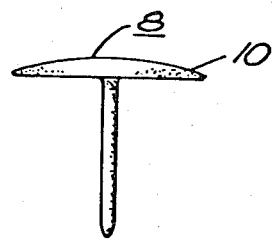
FIG. 1 illustrates one embodiment of an intra-uterine device useful in the practice of the present invention.

The group of preselected compounds of the present invention are the guanidines and in particular the aromatic monoguanidines, the aromatic diguanidines, and non-aromatic monoguanidines, and the non-aromatic diguanidines. The aromatic guanidines may be an aromatic monoguanidine of the general formula:

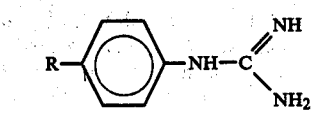

wherein:
R is a carbon chain with or without other elements (such as hydrogen, nitrogen, oxygen, sulfer, etc.); an aromatic group (such as benzene) with or without additional carbons, carbon chains, and other elements; a cyclic non-aromatic group (such as cyclohexane) with or without additional carbons, carbon chains, and other elements; or any of the above in combination; and

represents the benzene ring.

As preferred for utilization in the invention herein, there may be utilized an aromatic diguanidine of the general formula:

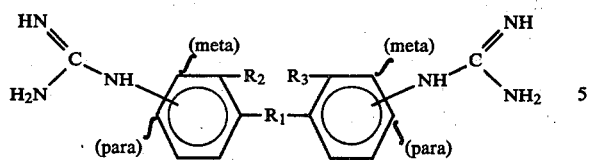

in which each guanidine group:

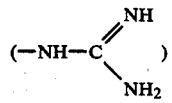

may be substituted in either a meta or para position with respect to $R_1$, and wherein:

$R_1$ is generally a hydrocarbon chain with or without ether or ester bonds to the benzene rings;

$R_2$ and $R_3$ can be hydrogen, chlorine, bromine, iodine, hydroxyl group, alkyl, or other group; and

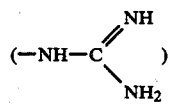

represents the benzene ring.

It is understood that the series of examples of aromatic diamidines in Table I, below, will also exemplify the aromatic diguanidines in every respect except that for the latter class of compounds guanidino groups:

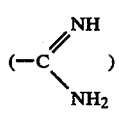

are substituted for amidino groups:

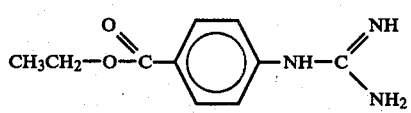

Two examples of aromatic monoguanidines are the following

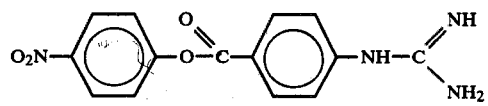

p-nitrophenyl-p′-guanidinobenzoate (commonly named NPGB). Two examples of aromatic diguanidines are the following:

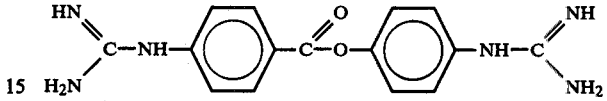

p-guanidinophenyl-p′-guanidinobenzoate and

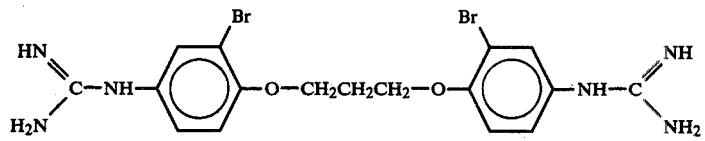

1,3 bis (2-bromo-4-guanidinophenoxy) propane.

[This last compound is analogous to dibromopropamidine (Table I) except that it is a diguanidine rather than a diamidine by virtue of the two guanidino groups:

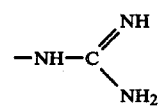

at both extremities of the molecule in place of the two amidino groups:

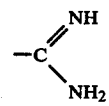

This diguanidine is assigned a chemical name in this application rather than a common or trivial name (such as "dibromopropaguanidine") because the compound and its analogs are not in common use and have not been previously given common names in the scientific literature.]

The non-aromatic guanidines may be a non-aromatic monoguanidine of the general formula:

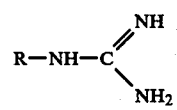

wherein R may represent a carbon chain with or without other elements (such as hydrogen, nitrogen, oxygen, sulfer, etc.); a cyclic non-aromatic group (such as cyclohexane) with or without additional carbons, carbon chains, and other elements; or any of the above in combination.

As preferred for utilization in the invention herein, there may be utilized a non-aromatic diguanidine of the general formula:

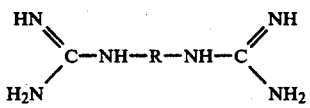

wherein:
R may represent a carbon chain with or without other elements (such as hydrogen, nitrogen, oxygen, sulfur, etc.); a cyclic aromatic group (such as cyclohexane) with or without additional carbons, carbon chains, and other elements; or any of the above in combination.

An example of a non-aromatic monoguanidine is the following:

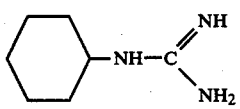

guanidinocyclohexane. An example of a non-aromatic diguanidine is the following:

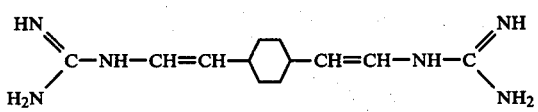

1,4-di(2-guanidinovinyl)cyclohexane.
In the above,

represents cyclohexane.

As set forth in my co-pending patent applications—Ser. Nos. 927,765, 928,093, and 928,106, Table I below lists particular aromatic diamidines useful in the practice of the inventions set forth therein, and useful in the practice of certain embodiments of the present invention wherein an amidine, such as the diamidines of Table I, are mixed with one or more guanidines to provide the drug of the present invention.

TABLE I
AROMATIC DIAMIDINES

| Drug Name | $R_1$ Carbon Chain | $R_2$ | $R_3$ | Relative Potency |
|---|---|---|---|---|
| Dibromopropamidine | $C_3H_6$ | Br | Br | 1.0 |
| Phenamidine | — | H | H | 0.2 |
| Octamidine | $C_8H_{16}$ | H | H | 2.6 |
| m-Pentamidine | $C_5H_{10}$ | H | H | 0.6 |
| Hexamidine | $C_6H_{12}$ | H | H | 1.6 |
| Dichlorohexamidine | $C_6H_{12}$ | Cl | Cl | 1.9 |
| Pentamidine | $C_5H_{10}$ | H | H | 2.4 |
| Monoiodohexamidine | $C_6H_{12}$ | I | H | 4.4 |
| Dibromopentamidine | $C_5H_{10}$ | Br | Br | 3.6 |
| Propamidine | $C_3H_6$ | H | H | 1.2 |
| Heptamidine | $C_7H_{14}$ | H | H | 1.9 |
| Diiodopentamidine | $C_5H_{10}$ | I | I | 6.8 |
| Diiodohexamidine | $C_6H_{12}$ | I | I | 7.5 |
| Butamidine | $C_4H_8$ | H | H | |
| Monochloropropamidine | $C_3H_6$ | Cl | H | |
| Monochlorobutamidine | $C_4H_8$ | Cl | H | |
| Monochloropentamidine | $C_5H_{10}$ | Cl | H | |
| Monochlorohexamidine | $C_6H_{12}$ | Cl | H | |
| Monochloroheptamidine | $C_7H_{14}$ | Cl | H | |

TABLE I-continued
AROMATIC DIAMIDINES

| Drug Name | $R_1$ Carbon Chain | $R_2$ | $R_3$ | Relative Potency |
|---|---|---|---|---|
| Monochloroctamidine | $C_8H_{16}$ | Cl | H | |
| Monochlorononamidine | $C_9H_{18}$ | Cl | H | |
| Monobromopropamidine | $C_3H_6$ | Br | H | |
| Monobromobutamidine | $C_4H_8$ | Br | H | |
| Monobromopentamidine | $C_5H_{10}$ | Br | H | |
| Monobromohexamidine | $C_6H_{12}$ | Br | H | |
| Monobromoheptamidine | $C_7H_{14}$ | Br | H | |
| Monobromoctamidine | $C_8H_{16}$ | Br | H | |
| Monobromononamidine | $C_9H_{18}$ | Br | H | |
| Moniodopropamidine | $C_3H_6$ | I | H | |
| Monoiodobutamidine | $C_4H_6$ | I | H | |
| Monoiodopentamidine | $C_5H_{10}$ | I | H | |
| Monoiodohexamidine | $C_6H_{12}$ | I | H | |
| Monoiodoheptamidine | $C_7H_{14}$ | I | H | |
| Monoiodoctamidine | $C_8H_{16}$ | I | H | |
| Monoiodononamidine | $C_9H_{18}$ | I | H | |
| Dichloropropamidine | $C_3H_6$ | Cl | Cl | |
| Dichlorobutamidine | $C_4H_8$ | Cl | Cl | |
| Dichloropentamidine | $C_5H_{10}$ | Cl | Cl | |
| Dichlorohexamidine | $C_6H_{12}$ | Cl | Cl | |
| Dichloroheptamidine | $C_7H_{14}$ | Cl | Cl | |
| Dichloroctamidine | $C_8H_{16}$ | Cl | Cl | |
| Dichlorononamidine | $C_9H_{19}$ | Cl | Cl | |
| Dibromopropamidine (already listed) | $C_3H_6$ | Br | Br | |
| Dibromobutamidine | $C_4H_8$ | Br | Br | |
| Dibromopentamidine | $C_5H_{10}$ | Br | Br | |
| Dibromohexamidine | $C_6H_{12}$ | Br | Br | |
| Dibromoheptamidine | $C_7H_{14}$ | Br | Br | |
| Dibromoctamidine | $C_8H_{16}$ | Br | Br | |
| Dibromononamidine | $C_9H_{18}$ | Br | Br | |
| Diiodopropamidine | $C_3H_6$ | I | I | |
| Diiodobutamidine | $C_4H_8$ | I | I | |
| Diiodopentamidine | $C_5H_{10}$ | I | I | |
| Dioodohexamidine | $C_6H_{12}$ | I | I | |
| Diiodoheptamidine | $C_7H_{14}$ | I | I | |
| Diiodooctamidine | $C_8H_{16}$ | I | I | |
| Diiodononamidine | $C_9H_{18}$ | I | I | |
| Monochloromonobromo-propamidine | $C_3H_6$ | Cl | Br | |
| Monochloromonobromo-butamidine | $C_4H_8$ | Cl | Br | |
| Monochloromonobromo-pentamidine | $C_5H_{10}$ | Cl | Br | |
| Monochloromonobromo-hexamidine | $C_6H_{12}$ | Cl | Br | |
| Monochloromonobromo-heptamidine | $C_7H_{14}$ | Cl | Br | |
| Monochloromonobromo-octamidine | $C_8H_{16}$ | Cl | Br | |
| Monochloromonobromo-nonamidine | $C_9H_{18}$ | Cl | Br | |
| Monochloromonobromo-propamidine | $C_3H_6$ | Cl | I | |
| Monochloromonobromo-butamidine | $C_4H_8$ | Cl | I | |
| Monochloromonobromo-pentamidine | $C_5H_{10}$ | Cl | I | |
| Monochloromonobromo-hexamidine | $C_6H_{12}$ | Cl | I | |
| Monochloromonoiido-heptamidine | $C_7H_{14}$ | Cl | I | |
| Monochloromonoiodo-octamidine | $C_8H_{16}$ | Cl | I | |
| Monochloromonoiodo-nonamidine | $C_9H_{18}$ | Cl | I | |
| Monobromomonoiodo-propamidine | $C_3H_6$ | Br | I | |
| Monobromomonoiodo-butamidine | $C_4H_8$ | Br | I | |
| Monobromomonoiodo-pentamidine | $C_5H_{10}$ | Br | I | |
| Monobromomonoiodo-hexamidine | $C_6H_{12}$ | Br | I | |
| Monobromomonoido-heptamidine | $C_7H_{14}$ | Br | I | |
| Monobromomonoiodo-octamidine | $C_8H_{16}$ | Br | I | |

TABLE I-continued
AROMATIC DIAMIDINES

| Drug Name | $R_1$ Carbon Chain | $R_2$ | $R_3$ | Relative Potency |
|---|---|---|---|---|
| Monobromomonoiodo-nonamidine | $C_9H_{18}$ | Br | I | |

In addition to the aromatic diguanidines, which, as noted above, are similar to the aromatic diamidines listed in Table I except for the substitution of the guanidine group for the amidine group in the drug and which, when trivial names have been assigned thereto will have trivial names similar to those shown in Table I other aromatic diguanidines, aromatic monoguanidines, non-aromatic monoguanidines and non-aromatic diguanidines may also be utilized in accordance with the principles of the present invention. The relative potency shown in Table I is expressed in relationship to dibromopropamidine, which has been discovered to be a highly potent fibrinolytic inhibitor. The numerical values are expressed as a reciprocal of the concentration of the drug producing the equivalent inhibition to the dibromopropamidine. Where no values for relative potency are listed such values have not been specifically determined.

The exact relative potency for the guanidines of the present invention has not yet been completely determined. However, those skilled in the art may rapidly determine the relative potency for any particular guanidine selected.

Figure 2:
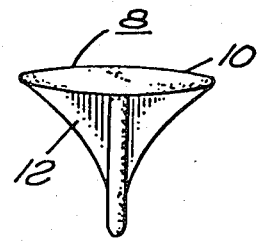
FIG. 2 illustrates another embodiment of an intra-uterine device useful in the practice of the present invention.
Figure 3:
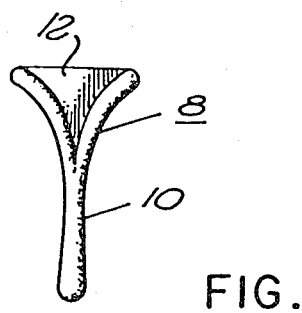
FIG. 3 illustrates another embodiment of an intra-uterine device useful in the practice of the present invention.
Figure 4:
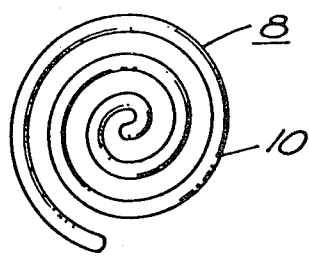
FIG. 4 illustrates another embodiment of an intra-uterine device useful in the practice of the present invention.
Figure 5:
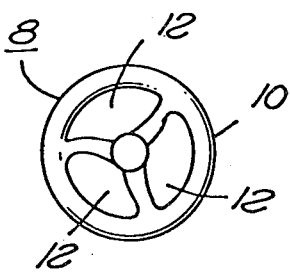
FIG. 5 illustrates another embodiment of an intra-uterine device useful in the practice of the present invention.

Referring now to the drawing, there are illustrated in FIGS. 1 through 5 thereof various well-known forms of intrauterine devices heretofore utilized. According to the principles of the present invention, many of the forms shown in FIGS. 1 through 5, as well as any other geometrical configurations of intrauterine devices, may be utilized in the practice of the present invention. Thus, the illustration of the known intrauterine devices illustrated in FIGS. 1 through 5 herein is not limiting to the principles of the present invention.

In the intrauterine devices shown in FIGS. 1 through 5, as well as in other configurations, the IUDs are generally comprised of a body member 8 of a polymer matrix having a relatively thick structural portion 10 and may or may not, as desired, be provided with one or more comparatively thin leaves 12. According to the principles of the present invention, in one embodiment thereof, the drug, which as noted above, may be one or more of the guanidines, or one or more guanidines mixed with one or more of the amidines, is mixed with the polymer matrix of the body member 8 in a predetermined ratio, depending upon the desired concentration of the drug within the uterus. The polymer of the body member 8 may be, for example:
1. low density polyethylene, or,
2. polyethyl vinyl acetate.

The ratio may be, for example, on the order of 10% to 50% by weight of the body member 8, depending upon the potency of the drug and the particular polymer matrix of the body member 8. Additionally, the shape, charge, and other characteristics of the drug molecule, such as its hydrophobicity, as well as similar characteristics of the polymer matrix, may be varied as desired to select the particular release rate of the drug from the body member 8 when placed within the uterus.

In another embodiment of the present invention, the drug may be provided as a biodegradable polymer or copolymer and mixed in the supporting polymer matrix of the body member 8 with selection of characteristics as above defined.

In another embodiment of the present invention, the drug is provided in a biodegradable polymer or copolymer form and it is covalently bonded to the polymer matrix of the body member 8 either or both within the body member 8 or on the surface thereon.

In any of the embodiments described above, there may also be provided, in another embodiment of the present invention, a biodegradable cross-linked polymer or copolymer coating of the drug bonded covalently to the surface of the polymer matrix of the body member 8 in order to provide a soft hydrogel coating thereover. Such a coating is likely to be particularly effective in aiding retention of the intrauterine device in the uterus during the time period soon after insertion thereof. The coating may be provided for some or all of the surface of the body member 8.

In another embodiment of the present invention, the drug is provided in a non-biodegradable monomer, dimer, or oligomer or a cross-linked polymer on the outer surface of the polymer matrix of the body member 8. This coating may be provided by covalent or other chemical bonding between drug molecules and the surface of the body member polymer matrix. Since the bleeding of the endometrium is at the interface between the endometrium and the intrauterine device, the solid phase enzyme inhibition provided by the drug at the point of contact between the endometrium and the intrauterine device can reduce the bleeding associated with utilizing an intrauterine device. In addition, the predetermined release of drug from the body member 8 will occur.

Further, since copper release has also been proven anti-conceptive in IUDs, some of the surface of the body member 8 may be provided with a coating of metallic copper such as wire, plating or the like. However, of course, such coating of metallic copper should not completely cover the body member 8 since that would prevent drug release.

It has been found that the drugs according to the present invention may provide an anti-conceptive effect. It is believed that this effect, which should enhance the anti-conceptive effect of the intrauterine device itself, is due to the activity of the drug and its action on the very early embryo and possibly on the sperm.

Further, it is believed yet an additional unexpected and surprising result may be obtained due to the anti-proteolytic action of the drug. This effect is a reduction in the pain and/or cramps and expulsion heretofore associated with utilization of intrauterine devices including medicated IUDs.

The range of concentrations necessary to provide the desired effects mentioned above depend, of course, upon the particular drug or combinations selected. For example, as noted in the above mentioned co-pending patent applications Ser. Nos. 927,765, 928,093 and 928,106, for dibromopropamidine introduced into the uterine cavity and endometrial tissue water, and with an endometrial water turnover rate of 200 milliliters per day and with complete distribution of the drug in the endometrial water turned over, an intrauterine release rate of 50 to 200 mcg per day would be expected to produce a concentration of dibromopropamidine in the range of 0.5 to $2.0 \times 10^{-6}$ moles per liter in endometrial water. Since, in general, there will be less than complete distribution of the drug into the endometrial water turned over each day, the concentration of the drug in the uterine cavity could reach much higher levels; for example, on the order of $10^{-6}$ to $10^{-4}$ moles per liter. This concentration range is sufficient to provide both the anti-fibrinolytic effects, as well as the anti-conceptive or anti-fertility effects desired, and also, it is believed, the reduction in pain, cramps and expulsion. With the above release rate (50–200 mcg per day), the known sizes of intrauterine devices currently available, and the amount of drug which can be incorporated into such devices, an effective life span of, for example, one to three years can be provided for such medicated devices.

At least one aromatic guanidine, NPGB as identified above, has an anti-fibrinolytic effect on the order of 100 times greater than that of dibromopropamidine (on a molar concentration basis). As little as 0.5 mcg to 2.0 mcg per day release of NPGB from a medicated IUD according to the principles of the present invention may be satisfactorily effective. Thus, the estimated range of daily release of the drug according to the present invention from a medicated IUD may be as low as, for example, 0.5 mcg to as high as 200 mcg, depending upon the particular constituents selected for inclusion in the drug. The useful life span of a device releasing, for example, 0.5 mcg per day may greatly exceed three years.

Those skilled in the art, of course, can readily determine the apropriate release rate desired for any drug or combination thereof which may be utilized according to the principles of the present invention and, in accordance with known principles, establish the desired release rate thereof to achieve effectiveness.

Further, those skilled in the art may find many variations and adaptations of the present invention and all such variations and adaptations thereof falling within the scope and spirit of the invention are intended to be covered by the appended claims.

In those embodiments of the present invention wherein a drug is provided as a coating on the surface of the IUD, the body member of the IUD may also incorporate a drug according to the principles of the present invention mixed therewith or the drug may be provide only in the coating. In those embodiments wherein a drug is provided as a coating on the surface of the IUD and a drug is also incorporated in the body member, the drug of the coating may be the same as the drug in the body member or they may be different drugs.

I claim:

1. A medicated intrauterine device of the type insertable into the uterus for retention therein for a predetermined time period and comprising, in combination, a uterus insertable body member comprising a polymer matrix having an external surface contacting the uterus, a coating on a first portion of said external surface of said body member comprising a drug, and said drug compromising at least a guanidine in one of a non-biodegradable monomer, non-biodegradable dimer, non-biodegradable oligomer and non-biodegradable, cross-linked polymer form and said drug chemically bonded to said surface of said polymer matrix.

2. The arrangement defined in claim 1 wherein:
said at least a guanidine of said drug selected from the class consisting of:
(a) aromatic monoguanidines;
(b) aromatic diguanidines;
(c) non-aromatic monoguanidines; and
(d) non-aromatic diguanidines.

3. The arrangement defined in claim 1 wherein:
said at least a guanidine of said drug selected from the class of aromatic monoguanidines of the group:

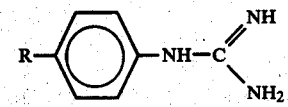

wherein R is selected from the class consisting of:
(a) a carbon chain free of other elements;
(b) a carbon chain with at least one other element;
(c) an aromatic group free of additional carbon atoms, carbon chains and other elements;
(d) an aromatic group with at least one addition selected from the class consisting of carbon atoms, carbon chains and other elements;
(e) a cyclic non-aromatic group free of additional carbon atoms, carbon chains and other elements;
(f) a cyclic non-aromatic group with at least one addition selected from the class consisting of carbon atoms, carbon chains, and other elements; and
(g) a combination of at least two of (a), (b), (c), (d), (e) and (f); and
wherein:

represents the benzene ring.

4. The arrangement defined in claim 1 wherein:
said at least a guanidine of said drug selected from the class of aromatic diguanidines of the group:

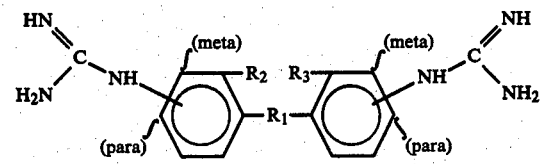

and wherein each guanidine group

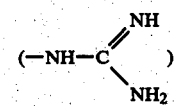

is in one of a meta or para position with respect to $R_1$, and in which:
$R_1$ is selected from the class consisting of:
(a) a hydrocarbon chain free of ether and ester bonds to the benzene ring; and
(b) a hydrocarbon chain having at least one bond selected from the class of ether bonds and ester bonds to the benzene ring;
$R_2$ and $R_3$ are selected from the class consisting of:
hydrogen, chlorine, bromine, iodine, hydroxyl group and alkyl group; and represents the benzene ring.

5. The arrangement defined in claim 1 wherein:
said at least a guanidine of said drug selected from the class of non-aromatic monoguanidines of the group:

$$R-NH-C(=NH)NH_2$$

wherein R is selected from the class consisting of:
(a) a carbon chain free of other elements;
(b) a carbon chain with at least one other element;
(c) a cyclic non-aromatic group free of additional carbon atoms, carbon chains and other elements;
(d) a cyclic non-aromatic group with at least one addition selected from the class consisting of carbon atoms, carbon chains and other elements;
(e) a combination of at least two of (a), (b), (c), and (d).

6. The arrangement defined in claim 1 wherein:
said at least a guanidine of said drug selected from the class consisting of non-aromatic diguanidines of the group:

$$H_2N-C(=NH)-NH-R-NH-C(=NH)-NH_2$$

wherein R is selected from the class consisting of:
(a) a carbon chain free of other elements;
(b) a carbon chain with at least one other element;
(c) a cyclic non-aromatic group free of additional carbon atoms, carbon chains and other elements;
(d) a cyclic non-aromatic group with at least one addition selected from the class consisting of carbon atoms, carbon chains and other elements;
(e) a combination of at least two of (a), (b), (c), and (d).

7. The arrangement defined in claim 1 wherein:
said at least a guanidine of said drug selected from the class consisting of:

$$CH_3CH_2-O-C(=O)-C_6H_4-NH-C(=NH)NH_2$$

ethyl-p-guanidinobenzoate, $$O_2N-C_6H_4-O-C(=O)-C_6H_4-NH-C(=NH)NH_2$$

p-nitrophenyl-p'-guanidinobenzoate (commonly named NPGB), $$H_2N-C(=NH)-NH-C_6H_4-C(=O)-O-C_6H_4-NH-C(=NH)NH_2$$

p-guanidinophenyl-p'-guanidinobenzoate, 1,3 bis (2-bromo-4-guanidinophenoxy) propane, guanidinocyclohexane, and 1,4-di(2-guanidinovinyl)cyclohexane.

8. The arrangement defined in claim 1 and further comprising:
a coating of copper on a second portion of said external surface of said body member.

9. A medicated intrauterine device of the type insertable in the uterus for retention therein for a predetermined time period and comprising, in combination;
a uterus insertable body member having an external surface contacting the uterus, and said body member comprising a polymer matrix and at least one drug with said polymer matrix and said at least one drug providing an anti-fibrinolytic effect, a reversible anti-fertility effect, and an anti-proteolytic effect, and said at least one drug comprising at least a guanidine, and said at least one drug and said polymer matrix selected to provide said at least one drug releasable at a predetermined rate from said body member to the uterus;
a coating on a first portion of said external surface of said body member comprising one of a biodegradable cross-linked polymer and biodegradable cross-linked copolymer form of a second drug, and said second drug comprising at least a guanidine, and said second drug covalently bonded to said surface of said polymer matrix;
said second drug selected from the class consisting of:
(a) a mixture of an amidine and a guanidine;

(b) a mixture of more than one amidine and a guanidine;
(c) a mixture of an amidine and more than one guanidine;
(d) a mixture of more than one amidine and more than one guanidine;
(e) a guanidine; and
(f) a mixture of more than one guanidine; and
said one drug selected from the class consisting of:
(a) a mixture of an amidine and a guanidine;
(b) a mixture of more than one amidine and a guanidine;
(c) a mixture of an amidine and more than one guanidine;
(d) a mixture of more than one amidine and more than one guanidine;
(e) a guanidine; and
(f) a mixture of more than one guanidine.

10. A medicated intrauterine device of the type insertable in the uterus for retention therein for a predetermined time period and comprising, in combination:
a uterus insertable body member having an external surface contacting the uterus, and said body member comprising a polymer matrix and at least one drug with said polymer matrix and said at least one drug providing an anti-fibrinolytic effect, a reversible anti-fertility effect, and an anti-proteolytic effect, and said at least one drug comprising at least a guanidine, and said at least one drug and said polymer matrix selected to provide said at least one drug releasable at a predetermined rate from said body member to the uterus; and
wherein said at least one drug comprises a soft hydrogel coating on a first portion of said external surface of said body member, and said at least one drug is in the form of one of a biodegradable cross-linked polymer and biodegradable copolymer covalently bonded to said body member.

11. The arrangement defined in claim 10 wherein said at least one drug is selected from the class consisting of:
(a) a mixture of an amidine and a guanidine;
(b) a mixture of more than one amidine and a guanidine;
(c) a mixture of an amidine and more than one guanidine;
(d) a mixture of more than one amidine and more than one guanidine;
(e) a guanidine; and
(f) a mixture of more than one guanidine.

12. The arrangement defined in claim 10 wherein said guanidine of said at least one drug is selected from the class consisting of:
(a) aromatic monoguanidines;
(b) aromatic diguanidines;
(c) non-aromatic monoguanidines; and
(d) non-aromatic diguanidines.

13. The arrangement defined in claim 10 wherein said at least one drug is selected form the class of aromatic monoguadines of the group:

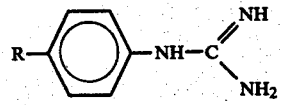

wherein R is selected from the class consisting of:
(a) a carbon chain free of other elements;
(b) a carbon chain with at least one other element;
(c) an aromatic group with at least one addition selected from the class consisting of carbon atoms, carbon chains and other elements;
(e) a cyclic non-aromatic group free of additional carbon atoms, carbon chains and other elements;
(f) a cyclic non-aromatic group with at least one addition selected from the class consisting of carbon atoms, carbon chains, and other elements; and
(g) a combination of at least two of (2) (b), (c), (d), (e) and (f); and
wherein:

represents the benzene ring.

14. The arrangement defined in claim 10 wherein said at least one drug is selected form the class of aromatic diguanidines of the group:

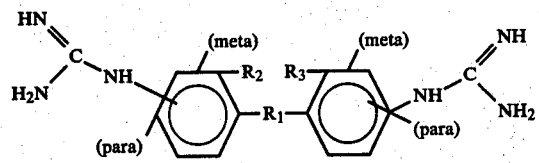

and wherein each guanidine group

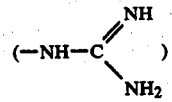

is in one of a meta or para position with respect to $R_1$, and in which:
$R_1$ is selected from the class consisting of:
(a) a hydrocarbon chain free of ether and ester bonds to the benzene ring; and
(b) a hydrocarbon chain having at least one bond selected from the class of ether bonds and ester bonds to the benzene ring;
$R_2$ and $R_3$ are selected from the class consisting of: hydrogen, chlorine, bromine, iodine, hydroxyl group and alkyl group; and

represents the benzene ring.

15. The arrangement defined in claim 10 wherein said at least one drug is selected from the class of non-aromatic monoguanidines fo the group:

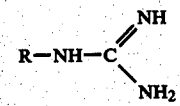

wherein R is selected from the class consisting of:

(a) a carbon chain free of other elements;
(b) a carbon chain with at least one other element;
(c) a cyclic non-aromatic group free of additional carbon atoms, carbon chains and other elements;
(d) a cyclic non-aromatic group with at least one addition selected from the class consisting of carbon atoms, carbon chains and other elements;
(e) a combination of at least two of (a), (b), (c), and (d).

16. The arrangement defined in claim 10 wherein said at least one drug is selected from the class consisting of non-aromatic diguanidines of the group:

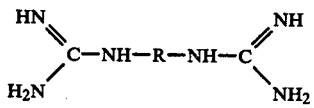

wherein R is selected from the class consisting of:
(a) a carbon chain free of other elements;
(b) a carbon chain with at least one other element;
(c) a cyclic non-aromatic group free of additional carbon atoms, carbon chains and other elements;
(d) a cyclic non-aromatic group with at least one addition selected from the class consisting of carbon atoms, carbon chains and other elements;
(e) a combination of at least two of (a), (b), (c), and (d).

17. The arrangement defined in claim 10 wherein said at least one drug is selected from the class consisting of:

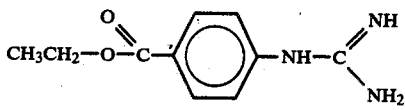

ethyl-p-guanidinobenzoate,

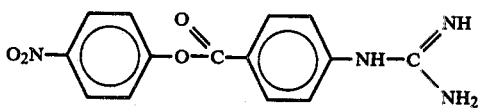

p-nitrophenyl-p'-guanidinobenzoate (commonly named NPGB),

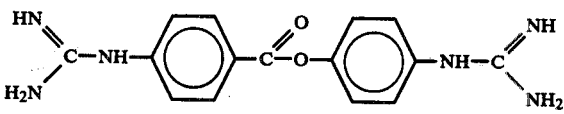

p-guanidinophenyl-p'-guanidinobenzoate,

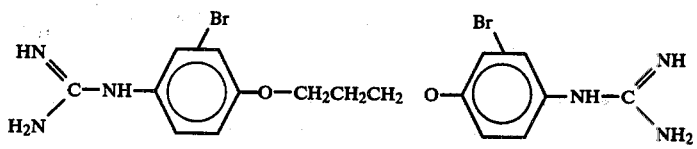

1,3 bis (20bromo-4-guanidinophenoxy) propane,

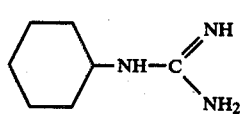

guanidinocyclohexane, and

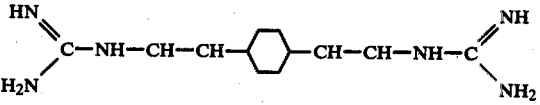

* * * * *